(12) United States Patent
Homölle et al.

(10) Patent No.: US 8,092,895 B2
(45) Date of Patent: Jan. 10, 2012

(54) LOOP TAPE FOR HOOK/EYE FASTENER

(75) Inventors: Dieter Homölle, Ochtrup (DE); Gerog Baldauf, Laer (DE)

(73) Assignee: Nordenia Deutschland Gronau GmbH, Gronau (DE)

( * ) Notice: Subject to any disclaimer, the term of this patent is extended or adjusted under 35 U.S.C. 154(b) by 704 days.

(21) Appl. No.: 12/131,160

(22) Filed: Jun. 2, 2008

(65) Prior Publication Data

US 2009/0068393 A1 Mar. 12, 2009

(30) Foreign Application Priority Data

Jun. 1, 2007 (EP) .................................... 07010876

(51) Int. Cl.
*B32B 3/06* (2006.01)
*B32B 33/00* (2006.01)
*A44B 18/00* (2006.01)
(52) U.S. Cl. ............................ 428/99; 428/95; 428/96
(58) Field of Classification Search .................... 428/92, 428/95, 96, 99, 100, 195.1, 198, 201, 203; 442/445, 447, 448, 451
See application file for complete search history.

(56) References Cited

U.S. PATENT DOCUMENTS

| | | | | |
|---|---|---|---|---|
| 4,643,932 A | 2/1987 | Daniels | ........................ | 428/100 |
| 5,957,908 A | 9/1999 | Kline | ............................ | 604/386 |
| 6,647,600 B1 * | 11/2003 | Jost et al. | ........................ | 24/442 |
| 6,869,659 B2 * | 3/2005 | Shepard et al. | ................. | 428/92 |
| 6,920,353 B1 * | 7/2005 | Heinze et al. | ...................... | 607/5 |
| 7,325,421 B2 | 2/2008 | Sasser | .............................. | 66/195 |
| 7,527,848 B2 * | 5/2009 | Baldauf | .......................... | 428/99 |
| 7,670,662 B2 * | 3/2010 | Baldauf | .......................... | 428/99 |
| 2002/0160143 A1 * | 10/2002 | Shepard et al. | ................. | 428/88 |
| 2004/0058121 A1 * | 3/2004 | Schriefer et al. | ................. | 428/99 |
| 2004/0099019 A1 * | 5/2004 | Sasser et al. | ..................... | 66/195 |
| 2004/0099020 A1 * | 5/2004 | Sasser et al. | ..................... | 66/203 |
| 2005/0166372 A1 * | 8/2005 | Shepard et al. | ................. | 24/442 |
| 2005/0181352 A1 * | 8/2005 | Shephard et al. | ............ | 434/428 |
| 2005/0208260 A1 * | 9/2005 | Baldauf | .......................... | 428/95 |
| 2006/0080810 A1 * | 4/2006 | Horn et al. | ...................... | 24/445 |
| 2006/0102037 A1 * | 5/2006 | Shepard et al. | ............... | 101/483 |
| 2006/0180272 A1 * | 8/2006 | Baldauf | ......................... | 156/290 |
| 2006/0182927 A1 * | 8/2006 | Baldauf | .......................... | 428/99 |
| 2010/0015386 A1 * | 1/2010 | Baldauf et al. | .................. | 428/99 |
| 2010/0132412 A1 * | 6/2010 | Baldauf et al. | .................. | 66/191 |
| 2010/0175825 A1 * | 7/2010 | Baldauf | ......................... | 156/269 |
| 2010/0298796 A1 * | 11/2010 | Horn et al. | ............... | 604/385.01 |

FOREIGN PATENT DOCUMENTS

EP 1690967 8/2006
EP 1842444 A1 * 10/2007

* cited by examiner

*Primary Examiner* — Cheryl Juska
(74) *Attorney, Agent, or Firm* — Andrew Wilford

(57) ABSTRACT

A laminated loop tape for a hook-and-loop fastener. The tape has a nonwoven textile support layer having an inner face, printing on the inner face, an at least partially transparent knitted cover layer having an inner face bearing on the support-layer inner face and an outer face provided with loops, and adhesive between the inner faces adhering the layers to each other.

7 Claims, 1 Drawing Sheet

LOOP TAPE FOR HOOK/EYE FASTENER

FIELD OF THE INVENTION

The present invention relates to a hook-and-loop fastener. More particularly this invention concerns a loop tape for use on a diaper or the like.

BACKGROUND OF THE INVENTION

A typical hook-and-loop fastener has one part or tape provided with a multiplicity of loops, that is U-shaped filaments anchored at both sides, and another part or tape formed with a multiplicity of J-shaped hooks that are anchored only at one point and that are flexible so they can engage in the hooks and hold the two tapes together. Such fasteners are particularly useful on clothing since they are easy to open and close, they can be laundered without harm, and they have no hard parts that can hurt the user. This makes them ideal for use on diapers, where the fact that their effectiveness is not affected detrimentally by moisture, creams, or powder is a big advantage.

Typically the female or loop tape is fixed to the front cuff area of the diaper. A mail hook tape attached laterally on the back of diaper completes the hook-and-loop fastener.

When used on a disposable diaper the hook-and-loop fastener is a particularly good location to provide printed matter. The textile material carrying the hooks should have the lowest possible mass/volume ratio so it can be made produced in a cost-effective manner. It should also be translucent so that printing on the surface of the support layer and the repeating pattern markings are visible for further processing of the tape. Despite of its low weight, the textile material must ensure a sufficient latching with hooks of the associated fastening tape. A sufficient number of freely movable loops and fibers, the function of which may not be influenced by any adhesion of the support layer to the textile cover layer, is required. Last but not least the material should appeal to the consumer. The aim is for optical and feel properties of a textile material.

Such a laminated loop tape is known from EP 1 690 967. The support layer is comprised of a single- or multi-layer plastic foil, polyolefins, polyester, polyamides, mixtures and copolymerisates of these polymers typically being used. The textile cover layer has a surface structure suitable for the anchoring hooks, and is adhered to the plastic foil. A good hook-and-loop effect is achieved by adhering the two layers together not over their full confronting faces, but only in uniformly spaced regions, leaving intervening regions that are not adhered together. This way the hooks are easy to latch to the surface loops and the fibers of the textile material in the adhesive-free areas. Despite a printing of the foil support layer, the appeal of the material still requires improvement. The textile effect of the material is lost with the shiny surface of the plastic foil. Furthermore, the foil is relatively stiff so that the laminated loop tape is perceived as a foreign body on the surface of the diaper. Finally, the laminated loop tape forms airtight areas, which are considered objectionable to the consumer, since the surrounding areas of the diaper are usually made of breathable material.

OBJECTS OF THE INVENTION

It is therefore an object of the present invention to provide an improved loop tape for a hook-and-eye fastener.

Another object is the provision of such an improved loop tape for a hook-and-eye fastener that overcomes the above-given disadvantages, in particular that is breathable.

A further object is to improve the feel, visual properties, and particularly air permeability of the laminated loop tape.

SUMMARY OF THE INVENTION

A laminated loop tape for a hook-and-loop fastener. The tape has according to the invention a nonwoven textile support layer having an inner face, printing on the inner face, an at least partially transparent knitted cover layer having an inner face bearing on the support-layer inner face and an outer face provided with loops, and adhesive between the inner faces adhering the layers to each other.

The support-layer inner face is printed by a rotary printing process that is characterized by its cost-effectiveness, despite fairly high setup costs for large printing volumes. Very high web speeds, and therefore also a large operational capacity can be achieved by a rotary printing process. The rotary printing process is preferably carried out by gravure printing techniques, where both direct and indirect gravure printing can be performed. In the case of direct gravure printing, the color is transferred to the substrate directly from recesses of the pressure cylinders, namely the ink-filled pockets thereof. In the case of indirect gravure printing, the color is initially applied to an impression roller typically made of rubber, and subsequently transferred from it to the nonwoven. While a uniform color application can be achieved by indirect gravure printing, direct gravure printing also enables the application of larger quantities of colors without any problems.

The term nonwovens means two-dimensional fibrous webs. The term includes both staple-fiber web fabric, and continuous filament fibers. Due to its greater tear strength, a woven fibrous web, or a multi-layer nonwoven material having at least one outer layer of woven fibrous web, is particularly suitable. A multi-layer nonwoven is preferred, having two outer layers of woven fibrous web (Spunbond S) sandwiching at least one layer of melt-blown fibers (Meltblown M). These multi-layer nonwoven materials having a layer structure SMS, SMMS, or SMMMS, are typically characterized by a uniform surface structure as opposed to pure fibrous web, thus having a greater printability. The nonwoven may consist of polyolefin fibers, polyamide fibers, polyester fibers, or fiber mixtures of these materials. The surface or areal density of the nonwoven utilized as the support layer is purposefully in a range between 10 $g/m^2$ and 30 $g/m^2$. The nonwoven utilized is preferably an SMS made of polypropylene within a weight range of 15 $g/m^2$.

Compared to a prior-art hook-and-loop fastener element whose the support layer is comprised of a plastic foil, the laminated loop tape according to the invention is characterized by greater flexibility, softness, and ability to breathe. The printed surface of the nonwoven shows through the partially transparent textile cover layer that has free loops created by knitting for the engagement of hook elements. The surface printing is protected from abrasion by the textile cover layer. The material has the appearance and the surface properties of a printed textile fabric. Furthermore, the support layer consisting of a nonwoven has a positive influence on the fastening effect of the hook elements dipping into the material, since the hook elements can also interact with the fiber portions of the nonwoven.

The printing of nonwoven textile materials (nonwovens) is known, and does not present any problems with cellulose substrates. The printing of nonwovens made of polyamide fibers, polyester fibers, and particularly of polyolefin fibers is more problematic. Conventional printing inks and dyes used on particularly fibrous polyolefin structures have a limited adhesion, which has an adverse effect on the wipe and abrasion resistance of a print image. A low wipe and abrasion resistance can be accepted with the laminated loop tape according to the invention, since the upper textile cover layer protects the print image. The printing is on the side facing the cover layer, and is protected on the bottom by the nonwoven and on the top by the textile cover layer.

In order to improve the printability and quality of the print image, the surface of the nonwoven to be printed may be pretreated. Bleeding of the printing ink is to be avoided by the nonwoven, since the rollers of the printing machine could otherwise be contaminated. Apart from the fact that such contamination requires extensive cleaning, dried on color residues may also contribute to defibration, or even to the destruction of a nonwoven so that pretreatment of the surface of the nonwoven to be printed is effective particularly also in order to avoid any bleeding of the printing ink. Finally, penetration of a lamination adhesive during bonding of the nonwoven to the cover layer should also be avoided.

Various possibilities of a pretreatment exist. A first embodiment provides a pretreatment of the surface of the nonwoven using a thixotropic primer. This primer is a layer that fixes the printing ink and contains inorganic fillers, such as silicon dioxide, titanium dioxide, calcium carbonate, calcined clay, or such, in a suitable binding agent, for improving the absorption and adhesion of the printing ink. The thixotropically adjusted primer behaves like a fluid under shear stress, and can be applied as a thin foil onto the fiber surface of the nonwoven due to its thixotropic properties. Without any shear stress, the primer has the properties of a solid material that adheres to the fiber surface. The thixotropic properties facilitate the application of the primer. Binding agents common in printing inks may be used as the primer, such as nitrocellulose (NC), polyvinyl butyral (PVB), or polyvinyl chloride (PVC). It is understood that as a binding agent, the primer may also contain resins that, for example, cross-link to a reaction medium that hardens at low temperatures. The primer may be applied at an amount of between 0.1 $g/m^2$ and 20 $g/m^2$, preferably between 0.5 $g/m^2$ and 2 $g/m^2$.

According to a further embodiment of the invention the surface of the nonwoven to be printed has a layer applied by spraying, which substantially forms a closed skin, and preferably has a layer thickness of less than 5 μm. A high-quality print image may be created on the closed surface of the sprayed-on layer, since the layer prevents bleeding of the printing ink.

Furthermore, a fine porous layer may be applied to the surface of the nonwoven to be printed for the absorption of the printing ink. Fine porous coatings are known as so-called "foam-coatings," and are utilized, for example, for sizing cotton textiles. The pretreatment of the nonwoven layers according to the invention with a fine porous layer improves the printability of the nonwoven layers particularly if they consist of polyolefin fibers. An improved print image can be obtained on pretreated nonwoven layers, the abrasion resistance and wipe resistance being simultaneously improved.

It is also within the scope of the invention that the surface of the nonwoven to be printed is provided with a layer applied by a wide-mouth extrusion nozzle. In such a so-called curtain coating method, the nonwoven passes through a thin curtain of melt that is dropping from the wide-mouth nozzle and that extends transversely of the travel direction of the passing web.

Additionally, or as an alternative to the described possibilities of pretreatment, the nonwoven is pretreated at its printed side, preferably by a corona discharge. Such a treatment can modify the surface structure of the fibers of the nonwoven such that the same can be more easily printed, or can be equipped with an additional coating. The nonwoven may also be pretreated using a plasma method, particularly a plasma coating process. Plasma polymerization processes are particularly suitable in which the surface is modified by the separation of certain materials from the plasma. For process technical reasons plasma methods are preferably used that can be carried out at atmospheric pressure since they do not require any extensive vacuum arrangements through which the nonwoven has to be guided.

The cover layer of the laminated loop tapes according to the invention is preferably comprised of a knit having weft filaments of yarns and warp filaments or yarns interconnected by knitting and with the loops integrated therein. The cover layer is glued to the support layer consisting of nonwoven, the adhesive being effectively applied in a pattern that is composed of adhesion areas and areas free of adhesive. The adhesion patterns described in above-cited EP 1 690 967 are particularly suited. The application of the adhesive is effectively carried out by the rotary printing method. The adhesion can be carried out using reactive polyurethane adhesives, or hot-melt adhesives. The adhesive application is preferably carried out in the form of stripe or dot patterns. The glued surface is 10 to 70%, preferably 60 to 40%. The proportion of the glued area and type and shape of the adhesive application depends on the typical opening forces with the use of the laminated loop tape in combination with a suitable hook-and-loop fastener. Preferably the applied adhesive forms cell patterns enclosed by the adhesive regions forming a frame. In addition to grid patterns, stripe and dot patterns have been proven to be particularly suited adhesive application patterns. It is critical in each case that the textile cover layer is not adhered to the nonwoven over its entire surface but that it instead has open cells that are free of glue in the adhesion free areas.

In a preferred further embodiment the section length of the laminated structure enclosed by one of the adhesive frames corresponds to the section length of the diaper fastener. The weft dimension that follows the repeating pattern and the application onto the diaper is achieved by a control stamp printed on the laminated material. The repeating pattern stamp may be visibly printed within the motif. The repeating pattern stamp may also be invisibly printed, e.g. using a dye that is visible under UV light only.

Fraying of the textile cover layer while being used with the loop hooks is prevented due to the complete edge adhesion of each individual diaper fastener. Fraying, e.g. the tearing off of the textile cover layer from the support layer, and thus the tearing of individual fibers and filaments, is an undesired side effect of partially glued laminated materials for mechanical diaper fasteners. Due to the fact that the loop hooks can engage more intensively in the non-glued open cells of the textile, than in the glued areas, the textile may tear when the hook-and-loop fastener is released, especially in the edge areas of the diaper fastener. The frame-shaped adhesion of the edge area prevents fraying.

A full-surface adhesive application is also possible. With lower opening forces, but higher demands of the laminated adhesion, full-surface adhesion is preferred over partial adhesion.

BRIEF DESCRIPTION OF THE DRAWING

The above and other objects, features, and advantages will become more readily apparent from the following description, reference being made to the accompanying drawing in which.

SPECIFIC DESCRIPTION

Figure 2:
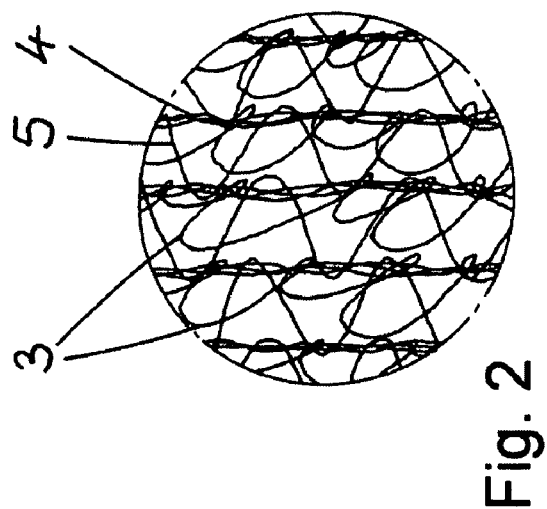
FIG. 2 is a large-scale view of a detail of the outer face of the cover layer.
Figure 1:
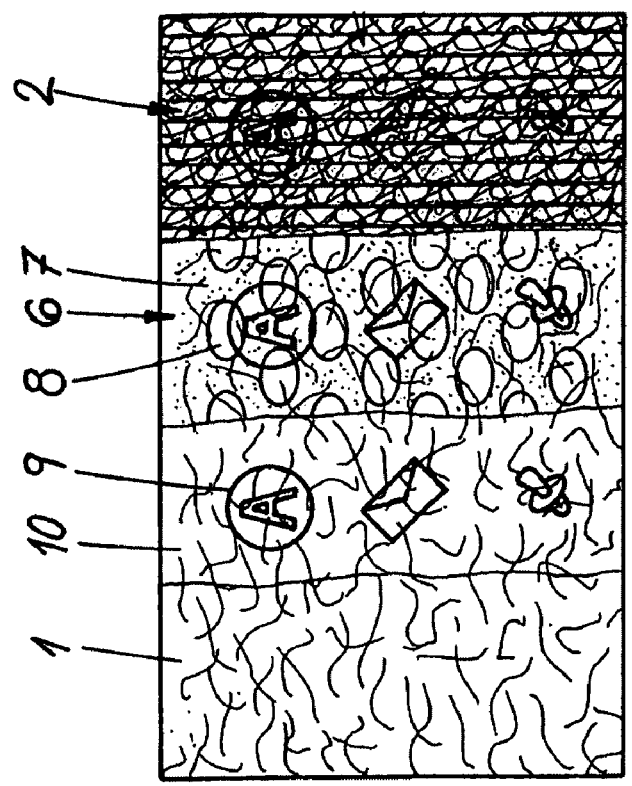
FIG. 1 is a top view of a tape with its various layers exposed from left to right.

As seen in FIG. 1 a laminated loop tape forms the female part of a hook-and-loop fastener, and in the case of the use as a diaper fastener, is attached, for example, in the front cuff area of the diaper. The laminated loop tape is comprised of a support layer 1 and a laminated on textile cover layer 2 having free loops 3 for the engagement of the hook elements. The cover layer is knitted and has warp strands 4 produced by knitting, having loops 3 incorporated therein, as well as weft yarns 5 (see FIG. 2). The cover layer 2 is glued to the support layer 1 by an adhesive 6 is applied in a pattern composed of adhesion areas 7 and areas 8 free of adhesive. In the illustrated embodiment the adhesive application has a pattern with a cell-shaped structure. It normally extends annularly or as a frame around the entire tape, or at least continuously along its longitudinal edges.

The support layer 1 is comprised of a nonwoven, preferably a fibrous web of continuous filament fibers, and is printed on its inner face facing the inner face of the cover layer 2 by the rotary printing method. The printing 9 of the nonwoven layer 1 is visible through the open structure of the textile cover layer 2.

The nonwoven support layer 1 is comprised of polyolefin fibers, preferably polypropylene fibers. This material can be printed without any pretreatment using only special inks containing solvents. In order to improve the printability, the surface of the nonwoven to be printed has been pretreated. The pretreatment in the form of a coating 10 is illustrated, which may be produced in different manners. It is within the scope of the invention that the surface of the nonwoven layer 1 is pretreated using a thixotropic primer, which fixes the printing ink, and which contains inorganic fillers, such as silicon dioxide, titanium dioxide, calcium carbonate, calcined clay, or such, in addition to a suitable binding agent, in order to improve the adhesion of the printing ink. The coating 10 may also be sprayed on the nonwoven layer 1 so as to form a closed skin on the nonwoven, and has a small layer thickness of, for example, less than 5 µm. Finally, the pretreatment may consist of the fact that a fine porous coating 10 is applied to the surface of the nonwoven to be printed for the absorption of the printing ink.

Thus as seen from left to right in FIG. 1 the nonwoven support layer 1 is first provided with the coating 10, then with the printing 9, then with the adhesive 6 in regions 7 leaving regions 8 clear, and finally the knit cover layer 2 is bonded atop it. These steps are all carried out in a continuous system with the layer 1 moving in a travel direction between rollers and through treatment stations doing the necessary steps. The coating 10 is sprayed on, formed by a plasma torch, or created by a curtain nozzle as mentioned above. The printing 9 is done by a roller, then the adhesive 6 is applied by another downstream roller, and a farther downstream roller presses the layer 2 down on the still-wet adhesive 6. This can all be done at high speed in a mass-production operation so as to minimize manufacturing costs.

We claim:

1. A laminated loop tape for a hook-and-loop fastener, the tape comprising:
   a nonwoven textile support layer having an inner face and an areal density of 10 to 30 g/m$^2$;
   a thixotropic primer on the support-layer inner face;
   rotary printing on the thixotropic primer on the inner face;
   an at least partially transparent knitted cover layer having an inner face bearing on the support-layer inner face and an outer face provided with loops; and
   adhesive between the inner faces adhering the layers to each other.

2. The laminated loop tape defined in claim 1 wherein the nonwoven layer is comprised of a fibrous web.

3. The laminated loop tape defined in claim 2 wherein the nonwoven layer has multiple layers at least one of which is the fibrous web.

4. The laminated loop tape defined in claim 1 wherein the knit cover layer has weft filaments and warp filaments.

5. The laminated loop tape defined in claim 1 wherein the adhesive is applied to the inner faces at spaced-apart regions defining intervening adhesive-free regions at which the faces can separate.

6. A laminated loop tape for a hook-and-loop fastener, the tape comprising:
   a nonwoven textile support layer having an inner face and an areal density of 10 to 30 g/m$^2$;
   a primer coating forming a substantially closed skin on the support-layer inner face and having a thickness of less than 5 µm;
   rotary printing on the primer coating;
   an at least partially transparent knitted cover layer having an inner face bearing on the support-layer inner face and an outer face provided with loops; and
   adhesive between the inner faces adhering the layers to each other.

7. A laminated loop tape for a hook-and-loop fastener, the tape comprising:
   a nonwoven textile support layer having an inner face and an areal density of 10 to 30 g/m$^2$;
   a fine porous coating on the support-layer inner face;
   rotary printing adhered to the fine porous coating;
   an at least partially transparent knitted cover layer having an inner face bearing on the support-layer inner face and an outer face provided with loops; and
   adhesive between the inner faces adhering the layers to each other.

* * * * *

UNITED STATES PATENT AND TRADEMARK OFFICE
CERTIFICATE OF CORRECTION

| | | |
|---|---|---|
| PATENT NO. | : 8,092,895 B2 | Page 1 of 1 |
| APPLICATION NO. | : 12/131160 | |
| DATED | : January 10, 2012 | |
| INVENTOR(S) | : Dieter Homölle et al. | |

It is certified that error appears in the above-identified patent and that said Letters Patent is hereby corrected as shown below:

Title Page item (75), the second inventor's name is correctly spelled as:

Georg BALDAUF

Signed and Sealed this
Thirteenth Day of March, 2012

David J. Kappos
*Director of the United States Patent and Trademark Office*